US008025874B2

(12) United States Patent
Bellot et al.

(10) Patent No.: US 8,025,874 B2
(45) Date of Patent: Sep. 27, 2011

(54) BACILLUS STRAINS USEFUL FOR ANIMAL ODOR CONTROL

(75) Inventors: Marianne Cain Bellot, Wauwatosa, WI (US); Keith J. Mertz, Neosho, WI (US); Thomas G. Rehberger, Wauwatosa, WI (US)

(73) Assignee: Danisco A/S, Copenhagen (DK)

( * ) Notice: Subject to any disclaimer, the term of this patent is extended or adjusted under 35 U.S.C. 154(b) by 149 days.

(21) Appl. No.: 12/425,546

(22) Filed: Apr. 17, 2009

(65) Prior Publication Data
US 2009/0275109 A1    Nov. 5, 2009

Related U.S. Application Data

(60) Provisional application No. 61/045,915, filed on Apr. 17, 2008.

(51) Int. Cl.
*A01N 63/00* (2006.01)
*C12N 1/20* (2006.01)

(52) U.S. Cl. ............... 424/93.3; 424/93.46; 424/93.462; 435/252.4; 435/252.5

(58) Field of Classification Search ........................ None
See application file for complete search history.

(56) References Cited

U.S. PATENT DOCUMENTS

| | | | |
|---|---|---|---|
| 2,906,622 A | 9/1959 | Lewis | |
| 2,942,977 A | 6/1960 | Lewis | |
| 3,892,846 A * | 7/1975 | Wortham | 424/76.6 |
| 4,820,531 A | 4/1989 | Tomes | |
| 4,919,936 A | 4/1990 | Iwanami | |
| 5,073,367 A | 12/1991 | Nguyen | |
| 5,478,557 A | 12/1995 | Nisbet | |
| 5,482,723 A | 1/1996 | Susaki | |
| 5,507,250 A | 4/1996 | Reddy | |
| 5,540,924 A | 7/1996 | Onishi | |
| 5,703,040 A | 12/1997 | Landolo | |
| 5,718,894 A | 2/1998 | Mann | |
| 5,830,993 A | 11/1998 | Biecha | |
| 5,840,318 A | 11/1998 | Marshall | |
| 5,879,719 A | 3/1999 | Valentine | |
| 5,945,333 A * | 8/1999 | Rehberger | 435/268 |
| 5,964,187 A | 10/1999 | Willis | |
| 5,965,128 A | 10/1999 | Doyle | |
| 6,008,195 A | 12/1999 | Selsted | |
| 6,156,355 A | 12/2000 | Shields, Jr. | |
| 6,207,411 B1 | 3/2001 | Ross | |
| 6,221,650 B1 * | 4/2001 | Rehberger | 435/252.4 |
| 6,346,422 B1 | 2/2002 | Butty | |
| 6,410,016 B2 | 6/2002 | Maruta | |
| 7,247,299 B2 | 7/2007 | Lin et al. | |
| 7,618,640 B2 | 11/2009 | Rehberger et al. | |
| 7,754,469 B2 * | 7/2010 | Baltzley et al. | 435/252.5 |
| 2002/0018770 A1 | 2/2002 | Maruta | |
| 2003/0099624 A1 | 5/2003 | Porubcan | |
| 2004/0170617 A1 | 9/2004 | Finegold | |
| 2005/0255092 A1 | 11/2005 | Rehberger | |
| 2006/0067924 A1 | 3/2006 | Lee et al. | |
| 2007/0202088 A1 | 8/2007 | Baltzley et al. | |
| 2009/0275109 A1 | 11/2009 | Bellot et al. | |
| 2009/0280090 A1 | 11/2009 | Rehberger et al. | |

FOREIGN PATENT DOCUMENTS

| | | |
|---|---|---|
| WO | 2004104175 | 5/2004 |
| WO | 2005112658 | 12/2005 |

OTHER PUBLICATIONS

Kim et al. "Aerobic nitrification-denitrification by heterothrophic Bacillus strains". Bioresource Technology. 2005, 96, pp. 1897-1906.*
Baker, G. C. et al, "Review and re-analysis of domain-specific 16S primers," Journal of Microbiological Methods (2003) 55:541-555.
Banach, S et al, "Prevalence, distribution and diversity of pathogenic *E. coli* in commercial turkey poult production," Presented at the Poultry Science Association Annual Meeting, Madison, WI, Jul. 2003.
Banach, S et al, "Prevalence, distribution and diversity of pathogenic *E. coli* in commercial turkey poult production," Poster #337, presented at the Poultry Science Association Annual Meeting, Madison, WI, Jul. 2003.
Barbosa, et al, "Applied and Environmental Microbiology," (Feb. 2005) vol. 71, 2:968-978.
Bembridge et al. "CD45RO expression on bovine T cells: relation to biological function," Immunology, (1995) 86:537-544.
Bertschinger, H U, "*Escherichia coli* infections," Diseases of Swine 8th Ed., Chap. 32, pp. 431-454, 1999.
Bikker, P. et al, "The influence of diet composition and an antimicrobial growth promoter on the growth response of weaned piglets to spray dried animal plasma." Livestock Prod. Sci. (2004) 86:201-208.
Billington et al., "*Clostridium perfringens* Type E animal enteritis isolates with highly conserved, silent enterotoxin gene sequences," Infect. Immun. (1998) 66(9):4531-4536.
Blood, D C, "Diseases caused by bacteria," Veterinary Medicine, 7th Ed., Bailliere, pp. 637-640, 1989.
Bosi, P. et al, "Effect of different spray dried plasmas on growth, ileal digestibility, nutrient deposition, immunity and health of early-weaned pigs challenged with *E. coli* K88," Asian-Aust. J. Anim. Sci. (2001) 14:1138-1143.
Bosi, P. et al, "Spray-dried plasma improves growth performance and reduces inflammatory status of weaned pigs challenged with enterotoxigenic *Escherichia coli* K88," J. Anim. Sci. (2004) 82:1764-1772.

(Continued)

*Primary Examiner* — Vera Afremova
(74) *Attorney, Agent, or Firm* — Whyte Hirschboeck Dudek S.C.

(57) ABSTRACT

A composition is provided that includes *Bacillus subtilis* 2084 (NRRL B-50013) or a strain having all of the identifying characteristics of the *Bacillus subtilis* 2084 (NRRL B-50013), *B. subtilis* 27 (NRRL B-50105) or a strain having all of the identifying characteristics of the *B. subtilis* 27 (NRRL B-50105), and *B. licheniformis* 21 (NRRL B-50134) or a strain having all of the identifying characteristics of the *B. licheniformis* 21 (NRRL B-50134). Animal bedding that includes the *Bacillus* strains is also provided, as well as a method of making the animal bedding. Also provided are methods of controlling odors from animal waste. A method of making a composition including the *Bacillus* strains is also provided.

23 Claims, 3 Drawing Sheets

OTHER PUBLICATIONS

Bosworth, B T et al. "Identification of toxin and pilus genes in porcine *Escherichia coli* using Polymerase Chain Reaction (PCR) with multiple primer pairs," Abstracts of the 97th General Meeting of the Am Society for Microbiology, May 4-8, 1997.

Brosius, J et al, "Complete nucleotide sequence of a 16S ribosomal RNA gene from *Escherichia coli*," Proc Natl Acad Sci USA 75(10:4801-4805, Oct. 1978.

Brown, D. C. et al, "The influence of different management systems and age on intestinal morphology, immune cell numbers and mucin production from goblet cells in post-weaning pigs," Vet. Immunol. Immunopath (2006a) 111:187-198.

Brown, D. C. et al, "Ontogeny of T lymphocytes and intestinal morphological characteristics in neonatal pigs at different ages in the postnatal period," J. Anim. Sci. (2006b) 84:567-578.

Carr, D et al, "Excessive mortality in market-age turkeys associated with cellulitis," Avian Disease 40:736-741, 1996.

Cera, K. R. et al, "Effect of age, weaning and post-weaning diet on small intestinal growth and small intestinal morphology in young swine," J. Anim. Sci. (1988) 66:574.

Coffey, R. et al, "The impact of environment and antimicrobial agents on the growth response of early weaned pigs to spray-dried porcine plasma," J. Anim. Sci. (1995) 73:2532-2539.

Cooper, V, "Diagnosis of neonatal pig diarrhea, "Vet Clinics N Am Food Animal Practice, 16(1):117-161 (2000).

Cromwell, G. L., "Antimicrobial and promicrobial agents. In: A. J. Lewis and L. L. Southern (eds.)," Swine Nutrition. p. 611. CRC Press, Boca Raton, FL (2001).

Cruywagen, C. W. et al, "Effect of *Lactobacillus acidophilus* supplementation of milk replacer on preweaning performance of calves," J. Dairy Sci. (1996) 79:483-486.

Davis. M. E. et al, "Effect of direct-fed microbial and antibiotic supplementation on gastrointestinal microflora, mucin histochemical characterization, and immune populations of weanling pigs," Livestock. Sci. (2007) 108:249-253.

Davis, M.E. et al, "Comparison of direct-fed microbial and antibiotic supplementation on innate and adaptive immune characteristics of weaning pigs," Reprod. Nutr. Dev. (2006) 46(Suppl.1):S63.

Davis, M. E. et al, "Rearing environment affects T lymphocyte populations within the systemic circulation and the gastrointestinal tract of young pigs.," Experimental Biology meeting abstracts [on CD ROM]. (2005) The FASEB Journal, 19, Abstract #43.7.

Davis, M.E. et al. "Dietary supplementation with phosphorylated mannans improves growth response and modulates immune function in weanling pigs," J. Anim. Sci. (2004) 82:1882-1891.

Davis, M. E. et al, "Inhalation Toxicology in the Equine Respiratory Tract," In: Equine Respiratory Diseases, P. Lekeux. International Veterinary Information Service (2002).

Dean-Nystrom, E et al, "Edema disease: a re-emerging problem?," Am Assoc of Swine Veterinarians, pp. 223-224, 2001.

Donald, J, "Treating poultry house floors to improve performance," The Poultry Engineering, Economics & Management Newsletter, Issue No. 23, 4 pgs, May 2003.

Donovan, D. C., "Growth and health of Holstein calves fed milk replacers supplemented with antibiotics or enteroguard," J. Dairy Sci. (2002) 85:947-950.

Dritz, S. et al, "Growth and microbial flora of nonmedicated, segregated, early weaned pigs from a commercial swine operation," JAVMA (1996) 208:711.

Dunlop, R. H., "Pathogenesis of ruminant lactic acidosis," Adv. Vet Sci. Comp Med. (1972) 16:259.

Ecological Laboratories, "Microbe-Lift equine products," EQ1, EQ2 and EQ3 (May 2001) (1 pg).

Elam, C. J. "Acidosis in feedlot cattle: Practical observations," J. Anim. Sci. (1976) 43:898.

Fangman, T. et al, "Segregated early weaning," Swine Health Prod. (1997) 5:195.

Francis, D, "Post-weaning *E. coli*-diagnosis, treatment, control, and its effect on subsequent growth performance," Am Assoc of Swine Veterinarians, 495-499, 2004.

Fritts, C A et al, "*Bacillus subtilis* C-3102 (Calsporin) improves live performance and microbioligical status of broiler chickens," Applied Poultry Science, Inc., 9:149-155, 2000.

Fuller, R., "Introduction. In: R. Fuller (Ed.). Probiotics 2: applications and practical aspects," Chapman and Hall, New York. (1997) p. 1.

Gaskins, H. R., "Intestinal bacteria and their influence on swine growth In: Austin J. Lewis and Lee L. Southern (Ed.)," Swine Nutrition 2nd Edition. (2001) p. 585-608.

Gebert, S. et al, "Development of a direct fed microbial to control pathogens associated with turkey poult production," Poult. Sci. (2006) 85(suppl. 1):71.

Gebert, S. et al, "Effect of a Bacillus-based direct-fed microbial on turkey poult performance and changes within the gastrointestinal microflora," J. Anim. Sci. (2007) 85(suppl. 1):249.

Grimes, J L et al, "Heat treatment of turkey litter for reuse as bedding," Int J of Poultry Science 2(5):287-292, 2003.

Hammer, C. et al, "Characterization of a colostrum replacer and a colostrum supplement containing IgG concentrate and growth factors," J. Dairy. Sci. (2004) 87:106-111.

Hatheway, C. L. "Toxigenic Clostridia," Clinical Microbiology Reviews (1990) 3(1):66-98.

Hofacre, C L et al, "Subcutaneous Clostridial infection in broilers," Case Report, Avian Diseases vol. 30(3):620-622, 1986.

Hong, H. A. et al, "The use of bacterial spore formers as probiotics," FEMS Microbiol. Rev. (2005) 29:813-835.

Hungate, R. E. et al, "Microbiological and physiological changes associated with acute indigestion in sheep," Cornell Vet. (1952) 42:423.

Janstova, B. et al, "Heat Resistance of *Bacillus* spp. Spores Isolated form Cow's Milk and Farm Environment," Acta Vet.. BRNO (2001) 70:179-184.

Jenny, B. F. et al, "Performance and fecal flora of calves fed a *Bacillus subtilis* concentrate," J. Dairy Sci. (1991) 74:1968-1973.

Jost B. H. et al, "Atypical cpb2 genes, encoding beta2-toxin in Clostridium perfringens isolates of nonporcine origin," Infect. Immun. (2005) 73:652-656.

Karunakaran, D et al, "Use of antibiotics and its impact on gut microflora in turkeys," Am Avian Path, Philadelphia, PA, Aug. 2004.

Karunakaran, D, "Microbioligical challenges of commercial turkey flocks and methods of control," Poster #PP51 presented at AAAP Symposium on Poultry Vaccines and Vaccination Practices, Jul. 15-17, 2002.

Kennedy, C et al, "The A-toxin of Clostridium septicum is essential for virulence," Molecular Microbiology, 57(5): 1357-1366, 2005.

King, M. et al, "Terminal restriction fragment length polymorphism analysis of gastrointestinal bacteria from conventional and segregated early weaned pigs: colonization and succession of putative pathogens and potential direct fed microbials," J. Anim Sci. (2005) 83 (Suppl. 1): 197.

Kyriakis, S. C. et al, "The effect of probiotic LSP 122 on the control of post-weaning diarrhea syndrome of piglets," Res. Vet. Sci. (1999) 67:223-228.

La Ragione R M et al, "*Bacillus subtilis* spores competitively exclude *Escherichia coli* 078:K80 in poultry," Vet Microbiol 79:133-142, 2001.

La Ragione, R. M. et al, "Competitive exclusion by *Bacillus subtilis* spores of *Salmonella enterica* serotype Enteritidis and Clostridium perfringens in young chickens," Vet. Microbiol,(2003) 94:245-256.

Lu, J et al, "Diversity and succession of the intestinal bacterial community of the maturing broiler chicken," Applied and Environmental Microbiology, 69(11):6816-6824, Nov. 2003.

Marquardt, R et al, "Passive protective effect of egg-yolk antibodies against enterotoxigenic *Escherichia coli* K88+ infection in neonatal and early-weaned piglets," FEMS Immunology and Med Microbiology 23:283-288, 1999.

Marsh, T. et al, "Terminal restriction fragment length polymorphism analysis web-based research tool for microbial community analysis," Appl Environ Microbiol (2000) 66:3616-3620.

Maxwell, Jr., C. V. et al, "Feeding Weanling Pigs. In: Austin J. Lewis and Lee L. Southern (Ed.)," Swine Nutrition 2nd Edition. (2001) p. 691-717.

McCracken, B. A. et al, "Diet-dependent and diet-independent metabolic responses underlie growth stasis of pigs at weaning," J. Nutr. (1995) 125, 2838-2845.

McDonough, S. P., "Enteric pathogens in intensively reared veal calves," Am. J. Vet. Res. (1994) 55(11):1516-1520.
McMillan, K., "Foal pneumonia: An Illinois survey," An Health and Nutrit 34 (1986).
Morrill, J. L. et al, "Plasma proteins and a probiotic as ingredients in milk replacer," J. Dairy Sci. (1995) 78:902-907.
Mouricout, M. A. et al, "Inhibition of mannose-resistant haemagglutination of sheep erythrocytes by enterotoxigenic *Escherichia coli* in the presence of plasma glycoprotein glycans," FEMS Microbiol. Lett. (1986) 37:145-149.
Muir, L.A. et al, "Prevention of induced lactic acidosis in cattle by thiopeptin," J. Anim. Sci. (1981) 52:635.
Muyzer, G et al, "Profiling of complex microbial populations by denaturing gradient gel electrophoresis analysis of polymerase chain reaction-amplified genes coding for 16S rRNA," Applied and Environmental Microbiology, 59 (3):695-700, Mar. 1993.
Nagy, G et al, "Genetic diversity among *Escherichia coli* isolates carrying f18 genes from pigs with porcine postweaning diarrhea and edema disease," J Clinical Microbiology 37:5:1642-1645, May 1999.
Nagy, G et al, "Genetic diversity among *Escherichia coli* isolates carrying f18 genes from pigs with porcine postweaning diarrhea and edema disease," J Clinical Microbiology 37:5:1642-1645, May 1999.
Niilo, L., "Clostridium perfringens in animal disease: a review of current knowledge," Can. Vet. J. (1980) 21:141-148.
Nollet, H. et al, "Protection of just weaned pigs against infection with F18+ *Escherichia coli* by non-immune plasma powder," Vet. Microbiol. (1999) 65:37-45.
Owens, F. N. et al, "Acidosis in cattle: a review," J. Anim. Sci. (1998) 76:275-286.
Parrott, D et al, "Molecular typing of hermolytic *Escherichia coli* isolated from swine," Paper 385 (1 pg), Intl Pig Vet Soc, 2002.
Patterson, J A et al, "Application of prebiotics and probiotics in poultry production," Poultry Science 82:626-631, 2003.
Perez-Bosque, A. et al, "Dietary plasma protein affects the immune response of weaned rats challenged with S. aureus," Superantigen B. J. Nutr. (2004) 134:2667-2672.
Power, E. G., "RAPD typing in microbiology—a technical review," J. Hosp. Infect. (1996) 34(4):247-265.
Rehberger, T, "Genome analysis of Propionibacterium freudenreichii by pulsed-field gel electrophoresis," Current Microbiology 27(1):21-25 Jul. 1993 (abstract).
Roche, K. C. et al, "Transforming growth factor beta-1 ameliorates intestinal epithelial barrier disruption by Cryptosporidium parvum in the absence of mucosal T lymphocytes," Infect. Immun. (2000) 68:5635-5644.
Roe, S, "Protein purification techniques," 2d Ed. Oxford U. Press, 172-175 (2001).
Slyter, L.L., "Influence of acidosis on rumen function," J. Anim. Sci. (1976) 43:910.
Snoeyenbos, G H, "Protecting chicks and poults from Salmonellae by oral administration of "normal" gut microflora," Avian Diseases 22(2):273-287, 1977.
Songer, J. G., "Clostridial enteric diseases of domestic animals," Clinical Microbiology Reviews (1996) 9(2):216-234.
Tam, N. K. M. et al, "The intestinal life cycle of *Bacillus subtilis* and close relatives," J. Bacteriol. (2006) 188:2692-2700.
Tang, M. et al, "Effect of segregated early weaning on postweaning small intestinal development in pigs," J. Anim. Sci. (1999) 77:3191.
Tanner, M. K. et al. "Respiratory and environmental effects of recycled phone book paper versus sawdust as bedding for horses," J Eq Vet Sci (1998) 468-476.
Tannock, G. W., "A special fondness for lactobacilli," Appl. Environ, Microbiol. (2004) 70:3189-3194.
Teo et al., "Applied & Environmental Microbiology," (Aug. 2005) vol. 71, 8:4185-4190.
Timmerman, H. M. et al, "Health and growth of veal calves fed milk replacers with or without probiotics," J. Dairy Sci. (2005) 88:2154-2165.
Torrallardona, D. et al, "Effect of fishmeal replacement with spray-dried plasma and colistin on intestinal structure, intestinal microbiology, and performance of weanling pigs challenged with *Escherichia coli* K99," J. Anim. Sci. (2003) 81:1220-1226.

Van Dijk, A. et al, "Growth performance of weanling pigs fed spray-dried animal plasma: a review," Livestock Production Science (2001a) 68:263-274.
Van Dijk, A. et al, "Growth performance and health status in weanling piglets fed spray-dried porcine plasmas under typical Northern European conditions," J. Anim. Physiol. Anim. Nutr. (Berl). (2002b) 86:17-25.
Vance, H. N., "A survey of the alimentary tract of cattle for Clostridium perfringens," Can. J. Comp. Med. Vet. Sci. (1967) 31:260-264.
Wattiau, P. et al, "A PCR test to identify *Bacillus subtilis* and closely related species and its application to the monitoring of wastewater biotreatment," Appl Microbiol Biotechnol 56:816-819, 2001.
Wattiau et al, Appl. Microbiol Biotechnol 2001, vol. 56, p. 816-819.
Wiard, T et al, "The effect of a biological litter treatment on Salmonella prevalence in turkey breeder flock litter," Poultry Science 80:127 (Suppl. 1):1-4, 2001.
Casey, P. G. et al, "A five-strain probiotic combination reduces pathogen shedding and alleviates disease signs in pigs challenged with Salmonella enterica serovar Typhimurium," Appl. Environ. Microbiol, (2007) 73:1858-1863.
Williams, J. G. et al, "DNA polymorphisms amplified by arbitrary primers are useful as genetic markers," Nucleic Acids Res. (1990) 18:6531-6535.
Willoughby, D H et al, "Periodic recurrence of gangrenous dermatitis associated with Clostridium speticum in a broiler chicken operation," J Vet Diagn Invest 8:259-261, 1996.
Wills, "*Escherichia coli* postweaning diarrhea," Vet Clinics N Am, pp. 138-140, 2000.
Wilson, M, "Segregated early weaning," Pig Lett. (1995) 15:17-20.
Wistuba et al, "Influence of fish oil supplementation on growth and immune system characteristics of cattle," J. Anim. Sci. (2005) 83:1097-1101.
Wu, X. Y. et al, "Characterization of mesophilic bacilli in feces of feedlot cattle," J. Appl. Microbiol. (2007) 102:872-879.
Yang, H. et al, "Effect of adding a bacillus based direct fed microbial on performance of nursery pigs fed diets with or without antibiotics," J. Anim. Sci. (2003).
Yang, W., "Effects of direct-fed microbial supplementation on ruminal acidosis, digestibility, and bacterial protein synthesis in continuous culture," Animal Feed Science and Technology, (2004) 114(4): 179-193.
Zhu, X Y, "16S rRNA-based analysis of microbiota from the cecum of broiler chickens," Applied and Environmental Microbiology, 68(1):124-137, Jan. 2002.
Zoetendal, E G et al, Molecular ecological analysis of the gastrointestinal microbiota: a review, J of Nutrition pp. 465-472, 2004.
Abe, F. et al, "Effect of administration of Bifidobacteria and lactic acid bacteria to newborn calves and piglets," J. Dairy Sci. (1995) 78:2838-2846.
Adami, A. et al, "Piglets fed from birth with the probiotic *Bacillus coagulans* as additive: zootechnical and microbiological aspects," Ann Microbiol Enzimol (1997) 47: 139-149.
Allison, M .J. et al, "Grain overload in cattle and sheep: Changes in microbial populations in the cecum and rumen," Amer. J. Vet Res. (1975) 36:181.
Awad, M M et al, "Synergistic effects of alpha-toxin and perfringolysin O in Clostridium perfringens-medicated gas gangrene," Infection & Immunity, 69(12):7904-7910, 2001.
Baker, A. et al, "Development of a *Bacillus subtilis* product for a large commercial swine farm to reduce Clostridium perfringens and Clostridium difficile in neonatal pigs," J. Anim. Sci. (2007) 85(suppl. 1):102.
Baker, G. C. et al, "Review and re-analysis of domain-specific 16S primers," Journal of Microbiological Methods (2003) 55:541-555.
Banach, S et al, "Prevalence, distribution and diversity of pathogenic *E. coli* in commercial turkey poult production," Presented at the Poultry Science Association Annual Meeting, Madison, WI, Jul. 2003.

Banach, S et al, "Prevalence, distribution and diversity of pathogenic *E. coli* in commercial turkey poult production," Poster #337, presented at the Poultry Science Association Annual Meeting, Madison, WI, Jul. 2003.

Barbosa, et al, "Applied and Environmental Microbiology," (Feb. 2005) vol. 71, 2:968-978.

Bembridge et al. "CD45RO expression on bovine T cells: relation to biological function," Immunology, (1995) 86:537-544.

Bertschinger, H U, "*Escherichia coli* infections," Diseases of Swine 8th Ed., Chap. 32, pp. 431-454, 1999.

Bikker, P. et al, "The influence of diet composition and an antimicrobial growth promoter on the growth response of weaned piglets to spray dried animal plasma." Livestock Prod. Sci. (2004) 86:201-208.

Billington et al., "Clostridium perfringens Type E animal enteritis isolates with highly conserved, silent enterotoxin gene sequences," Infect. Immun. (1998) 66(9):4531-4536.

Blood, D C, "Diseases caused by bacteria," Veterinary Medicine, 7th Ed., Bailliere, pp. 637-640, 1989.

Bosi, P. et al, "Effect of different spray dried plasmas on growth, ileal digestibility, nutrient deposition, immunity and health of early-weaned pigs challenged with *E. coli* K88," Asian-Aust. J. Anim. Sci. (2001) 14:1138-1143.

Bosi, P. et al, "Spray-dried plasma improves growth performance and reduces inflammatory status of weaned pigs challenged with enterotoxigenic *Escherichia coli* K88," J. Anim. Sci. (2004) 82:1764-1772.

Bosworth, B T et al. "Identification of toxin and pilus genes in porcine *Escherichia coli* using Polymerase Chain Reaction (PCR) with multiple primer pairs," Abstracts of the 97th General Meeting of the Am Society for Microbiology, May 4-8, 1997.

Brosius, J et al, "Complete nucleotide sequence of a 16S ribosomal RNA gene from *Escherichia coli*," Proc Natl Acad Sci USA 75(10:4801-4805, Oct. 1978.

Brown, D. C. et al, "The influence of different management systems and age on intestinal morphology, immune cell numbers and mucin production from goblet cells in post-weaning pigs," Vet. Immunol. Immunopath (2006a) 111:187-198.

Brown, D. C. et al, "Ontogeny of T lymphocytes and intestinal morphological characteristics in neonatal pigs at different ages in the postnatal period," J. Anim. Sci. (2006b) 84:567-578.

Carr, D et al, "Excessive mortality in market-age turkeys associated with cellulitis," Avian Disease 40:736-741, 1996.

Cera, K. R. et al, "Effect of age, weaning and post-weaning diet on small intestinal growth and small intestinal morphology in young swine," J. Anim. Sci. (1988) 66:574.

Coffey, R. et al, "The impact of environment and antimicrobial agents on the growth response of early weaned pigs to spray-dried porcine plasma," J. Anim. Sci. (1995) 73:2532-2539.

Cooper, V, "Diagnosis of neonatal pig diarrhea, "Vet Clinics N. Am Food Animal Practice, 16(1):117-161 (2000).

Cromwell, G. L., "Antimicrobial and promicrobial agents. In: A. J. Lewis and L. L. Southern (eds.)," Swine Nutrition. p. 611. CRC Press, Boca Raton, FL (2001).

Cruywagen, C. W. et al, "Effect of *Lactobacillus acidophilus* supplementation of milk replacer on preweaning performance of calves," J. Dairy Sci. (1996) 79:483-486.

Davis. M. E. et al, "Effect of direct-fed microbial and antibiotic supplementation on gastrointestinal microflora, mucin histochemical characterization, and immune populations of weanling pigs," Livestock. Sci. (2007) 108:249-253.

Davis, M.E. et al, "Comparison of direct-fed microbial and antibiotic supplementation on innate and adaptive immune characteristics of weaning pigs," Reprod. Nutr. Dev. (2006) 46(Suppl.1):S63.

Davis, M. E. et al, "Rearing environment affects T lymphocyte populations within the systemic circulation and the gastrointestinal tract of young pigs.," Experimental Biology meeting abstracts [on CD ROM]. (2005) The FASEB Journal, 19, Abstract #43.7.

Davis, M.E. et al. "Dietary supplementation with phosphorylated mannans improves growth response and modulates immune function in weanling pigs," J. Anim. Sci. (2004) 82:1882-1891.

Davis, M. E. et al, "Inhalation Toxicology in the Equine Respiratory Tract," In: Equine Respiratory Diseases, P. Lekeux. International Veterinary Information Service (2002).

Dean-Nystrom, E et al, "Edema disease: a re-emerging problem?," Am Assoc of Swine Veterinarians, pp. 223-224, 2001.

Donald, J, "Treating poultry house floors to improve performance," The Poultry Engineering, Economics & Management Newsletter, Issue No. 23, 4 pgs, May 2003.

Donovan, D. C., "Growth and health of Holstein calves fed milk replacers supplemented with antibiotics or enteroguard," J. Dairy Sci. (2002) 85:947-950.

Dritz, S. et al, "Growth and microbial flora of nonmedicated, segregated, early weaned pigs from a commercial swine operation," JAVMA (1996) 208:711.

Dunlop, R. H., "Pathogenesis of ruminant lactic acidosis," Adv. Vet Sci. Comp Med. (1972) 16:259.

Ecological Laboratories, "Microbe-Lift equine products," EQ1, EQ2 and EQ3 (May 2001) (1 pg).

Elam, C. J. "Acidosis in feedlot cattle: Practical observations," J. Anim. Sci. (1976) 43:898.

Fangman, T. et al, "Segregated early weaning," Swine Health Prod. (1997) 5:195.

Francis, D, "Post-weaning *E. coli*-diagnosis, treatment, control, and its effect on subsequent growth performance," Am Assoc of Swine Veterinarians, 495-499, 2004.

Fritts, C A et al, "*Bacillus subtilis* C-3102 (Calsporin) improves live performance and microbioligical status of broiler chickens," Applied Poultry Science, Inc., 9:149-155, 2000.

Fuller, R., "Introduction. In: R. Fuller (Ed.). Probiotics 2: applications and practical aspects," Chapman and Hall, New York. (1997) p. 1.

Gaskins, H. R., "Intestinal bacteria and their influence on swine growth In: Austin J. Lewis and Lee L. Southern (Ed.)," Swine Nutrition 2nd Edition. (2001) p. 585-608.

Gebert, S. et al, "Development of a direct fed microbial to control pathogens associated with turkey poult production," Poult. Sci. (2006) 85(suppl. 1):71.

Gebert, S. et al, "Effect of a Bacillus-based direct-fed microbial on turkey poult performance and changes within the gastrointestinal microflora," J. Anim. Sci. (2007) 85(suppl. 1):249.

Grimes, J L et al, "Heat treatment of turkey litter for reuse as bedding," Int J of Poultry Science 2(5):287-292, 2003.

Hammer, C. et al, "Characterization of a colostrum replacer and a colostrum supplement containing IgG concentrate and growth factors," J. Dairy. Sci. (2004) 87:106-111.

Hatheway, C. L. "Toxigenic Clostridia," Clinical Microbiology Reviews (1990) 3(1):66-98.

Clean Air "HM Composter and Odor Eliminator," (1 pg), at least as early as Apr. 16, 2007.

"Copy for immediate release" 'Online! Jan. 13, 2005, pp. 1-2 XP002342562, retrieved from the Internet: URL: http://www.agtechproducts.com/press/DSM_Market_Microsource.pdf>, p. 1, line 1-line 15, p. 2, paragraph 4-last paragraph.

A multiple-strain product, commercially sold as Microsource direct-fed microbial, containing Bacillus strains *Bacillus subtilis* 27(BS27), *Bacillus licheniformis* (previously thought to be B. amyloliquefaciens) 842, and *Bacillus licheniformis* 21 (BI 21) has been sold at least as early as Jan. 1, 2000 to improve the decomposition of stored swine manure.

Gyles, C., Workshop #4: Enteric Diseases of Nursery Pigs, pp. 29-41, AASV 32nd Annual Meeting (2001), Nashville, Tenn.

NCBI gene bank accession #M59107, Apr. 27, 1993.

NCBI gene bank accession #X73447, Jan. 9, 2004.

"Nonruminant Nutrition: weanling Pigs-additives" Online! 2004, pp. 25-28 XP002342561, Retrieved from the Internet: URL:http//www.fass.org/2004/abstracts/25.PDF> p. 26, col. 2, paragraph 3-5, J. Anim. Sci. Vol. 82, Supp. 1/ J. Dairy Sci. vol. 87 Suppl. 1 / Poultry Sci. vol. 83, Supp 1.

Pyne, E et al, Prevalence and genetic diversity of Clostridum perfringens isolated from commercial turkey houses, Abstract #432 in Abstracts of papers (2008).

Stable Fresh TM 1:3 concentrate, "An all natural USDA approved concentrate that eliminates stall odors for just pennies per day, per stall," Sterling Creek Enterprises (2 pgs), at least as early as Apr. 16, 2007.

"Table of Contents" Online! 2004, p. 1-4, XP002342560, retrieved from the Internet: URL:http://www.fass.org/2004/abstracts/>, p. 1, lines 1-14, Poster Presitations, Jul. 26, 2004.

"Watt Feed E-News Feb. 8, 2005" 'Online! Feb. 8, 2005, pp. 1-6, XP002342563, retrieved from the Internet: URL:http://www.wattnet.com/Newsletters/feed/htm/FEBFEED05.htm.

Wiard, T et al, Application of plating enumerations and denaturing gradient gel electrophoresis to study turkey poult gastrointestinal tract bacterial diversity, (4 pgs) presented at the Poultry Science Assoc meeting, Madison, WI 2003.

Wiard, T et al, "Application of plating enumerations and denaturing gradient gel electrophoresis to study turkey poult gastrointestinal tract bacterial diversity," Poster #244 and its abstract, presented at the Poultry Science Assoc meeting, Madison, WI 2003.

Sale: Agtech Products, Inc. purchased strain *Bacillus subtilis* 2084 from a third party. At least as early as Sep. 10, 2004.

Sale: Agtech Products, Inc. purchased strain *Bacillus licheniformis* 21 from a third party. At least as early as Jan. 30, 2007.

\* cited by examiner

BACILLUS STRAINS USEFUL FOR ANIMAL ODOR CONTROL

CROSS-REFERENCE TO RELATED APPLICATIONS

This application claims priority under 35 U.S.C. §119(e) to U.S. Provisional Patent Application No. 61/045,915, filed Apr. 17, 2008, the entirety of which is incorporated by reference herein.

FIELD OF THE INVENTION

The invention relates to controlling odors associated with animals. More particularly, the invention relates to *Bacillus* strains for controlling odors associated with the bedding or other environment of animals, such as horses, guinea pigs, and the like and methods of making and using the *Bacillus* strains.

BACKGROUND OF THE INVENTION

Animals, including, but not limited to, companion animals, livestock, laboratory animals, working animals, and sport animals, generate odors that most people find offensive, especially when the odors are strong. For animals kept outdoors, this can lead to problems with neighbors, staff that work with the animals, and owners of the animals. Odors from animals kept indoors can aggravate the animal's owners, those living in the same household of the indoor animal, and visitors to the household where the animal is kept.

Ammonia and other odors coming from farms, such as horse farms, can aggravate neighbors, especially in residential areas. The ability to effectively control and alleviate waste odors associated with equine in urban areas provides a healthier living environment and helps horse enthusiasts to maintain good relationships with their neighbors.

Ammonia negatively affects the health of stabled horses worldwide. Even long-term, low level exposure to ammonia can affect a horse's respiratory health and immune response. (Davis, M. S. Foster, W. M. "Inhalation Toxicology in the Equine Respiratory Tract." In: Equine Respiratory Disease, P. Lekeus. International Veterinary Information Service, 2002). Horse bedding consists of materials such as straw, sand and other material. Wood shavings are commonly used as bedding material to help absorb urine and provide a surface for easy clean up. The condition or quality of bedding in equine stalls can be affected by a number of factors including frequency of clean-out, ventilation, moisture and temperature. Due to the health problems associated with high levels of ammonia, proper barn management is crucial. Daily cleaning, good ventilation and complete clean-out of stalls when bedding is too soiled are essential to control ammonia exposure. Due to the cost of bedding materials, most horse owners clean stalls daily but prefer not to strip stalls on a regular basis. There is great value in extending the bedding life and the amount of time that bedding remains in the stall. By reducing the ammonia odors in the bedding, bedding life can be extended, resulting in a great cost savings.

There are more horses in the United States currently than there were in the 1800's, many of them kept in urban areas. In this setting, the manure and urine from horses can be offensive to non-horse owners and can be a problem for municipal landfills. Ammonia production can also cause performance loss in competitive horse events like horse racing.

Some products to treat horse waste material are available, but most are chemically based and only provide short term relief of odors and no increased digestion of solid waste. Some products control ammonia with absorbents, such as clay and zeolite. These products function by providing negatively charged exchange sites to attract ammonium ions. In this process, more weakly bound ions such as hydrogen and sodium are replaced by ammonium ions, reduction the total concentration of ammonia in solution. These products also bind water, reducing the microbial activity and therefore the breakdown of urea to ammonia. Other products control ammonia via yucca additives and fragrances that simply mask the odor. Ammonia negatively affects the health of caged small animal pets as well.

Guinea pigs, hamsters, rats and other small animals need soft clean bedding that is changed frequently in order for the animal to stay in top health. Bedding is replaced to keep down ammonia, and to keep small animals and the cage clean. Ammonia is a component of urine. In high concentrations not only does it smell offensive to humans, but it can eventually lead to respiratory problems for the small animals. Breathing concentrated ammonia will damage their lungs, burn their esophagus and create other health problems. Therefore, reducing ammonia levels is important for small animals. There is also a great value and need in extending bedding life.

Ammonia concentrations in poorly ventilated horse barns and cages can rise to levels potentially harmful to the equine and small animal respiratory tract. High levels of ammonia have been associated with foal pneumonia (McMillan K: Foal pneumonia: An Illinois survey. *An Health and Nutrit* 1986; 34). High levels of ammonia may also predispose horses to chronic obstructive pulmonary disease. (Tanner M K, Swinker A M, Traub-Dargatz J L, Stiffler L A, McCue P M, Vanderwall D K, Johnson K E: Respiratory and environmental effects of recycled phone book paper versus sawdust as bedding for horses. *J Eq Vet Sci* 1998; 468-476). Ammonia and odor smells coming from horse farms can aggravate neighbors, especially in residential areas.

The ammonia present in equine facilities and small animal cages is the product of microbial decomposition of excreted nitrogenous compounds. This includes urea, nonabsorbed proteins, amino acids, and nonprotein nitrogen present in the diet.

In view of the foregoing, it would be desirable to provide one or more *Bacillus* strains to treat or prevent animal odors and to provide animal bedding including one or more of these strains, methods of using the *Bacillus* strains and animal bedding treated with the *Bacillus* strains.

SUMMARY OF THE INVENTION

The invention, which is defined by the claims set out at the end of this disclosure, is intended to solve at least some of the problems noted above. A composition is provided that includes *Bacillus subtilis* 2084 (NRRL B-50013) or a strain having all of the identifying characteristics of the *Bacillus subtilis* 2084 (NRRL B-50013), *B. subtilis* 27 (NRRL B-50105) or a strain having all of the identifying characteristics of the *B. subtilis* 27 (NRRL B-50105), and *B. licheniformis* 21 (NRRL B-50134) or a strain having all of the identifying characteristics of the *B. licheniformis* 21 (NRRL B-50134).

In some embodiments of the composition, at least one carrier capable of binding ammonia is included with the *Bacillus* strains. In some embodiments of the composition, at least one water-soluble carrier is included with the *Bacillus* strains.

Animal bedding that includes the *Bacillus* strains is also provided, as is a method of making the animal bedding.

Also provided are methods of controlling odors from animal waste. In some embodiments of these methods, at least one carrier capable of binding ammonia and the *Bacillus* strains are used to control odors. In some embodiments of these methods, at least one water-soluble carrier and the *Bacillus* strains are used to control odors.

A method of making a composition is also provided. In it, each of *Bacillus subtilis* 2084 (NRRL B-50013) or a strain having all of the identifying characteristics of the *Bacillus subtilis* 2084 (NRRL B-50013), *B. subtilis* 27 (NRRL B-50105) or a strain having all of the identifying characteristics of the *B. subtilis* 27 (NRRL B-50105), and *B. licheniformis* 21 (NRRL B-50134) or a strain having all of the identifying characteristics of the *B. licheniformis* 21 (NRRL B-50134) is grown in a broth. Each of the strains is separated from its broth to make the composition.

BRIEF DESCRIPTION OF THE DRAWINGS

Preferred exemplary embodiments described herein are illustrated in the accompanying drawings, in which like reference numerals represent like parts throughout and in which.

Figure 1:
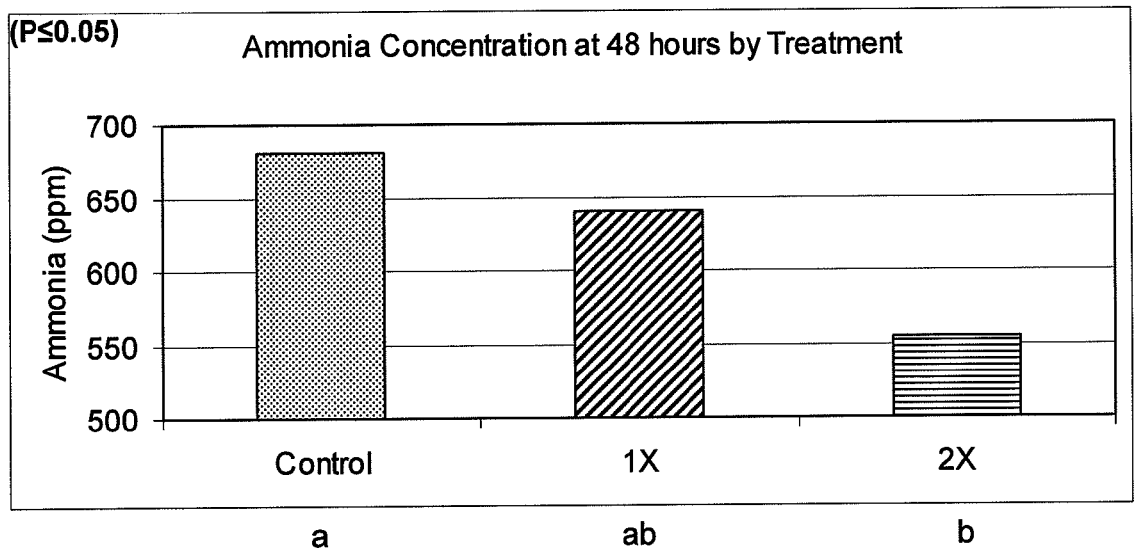
FIG. 1 is a graph of ammonia concentration at 48 hours, with bars with different letters being significantly different.

Before explaining embodiments described herein in detail, it is to be understood that the invention is not limited in its application to the details of construction and the arrangement of the components set forth in the following description or illustrated in the drawings. The invention is capable of other embodiments or being practiced or carried out in various ways. Also, it is to be understood that the phraseology and terminology employed herein is for the purpose of description and should not be regarded as limiting.

DETAILED DESCRIPTION

Provided herein are combinations of three *Bacillus* strains that can be used to form odor-controlling compositions for controlling ammonia and other odors from non-human animals. Laboratory studies have shown a 50-60% reduction in ammonia on wood shavings treated with one or more compositions provided herein. Additional benefits of using the compositions to treat or prevent animal odors can include one or more of the following.

Compositions:

*Bacillus* strains have many qualities that make them useful for treating and preventing animal odors. For example, *Bacillus* strains produce extracellular enzymes, such as proteases, amylases, and cellulase. In addition, *Bacillus* strains produce antimicrobial factors, such as gramicidin, subtilin, bacitracin, and polymyxin. Several *Bacillus* species also have GRAS status, i.e., they are generally recognized as safe by the US Food and Drug Administration and are also approved for use in animal feed by the Association of American Feed Control Officials (AAFCO). All *B. subtilis* strains are GRAS.

The *Bacillus* strains described herein are aerobic and facultative sporeformers and thus, are stable. *Bacillus* species are the only sporeformers that are considered GRAS. *Bacillus* strains preferably are used as spores. When rehydrated, with liquid containing nutrients, the *Bacillus* strains can go into the vegetative state. However, when again dehydrated or without enough nutrients, the *Bacillus* strains will go back to spores.

*Bacillus* strains found to be useful in the compositions provided herein include *B. subtilis* strains 2084 and 27 and *B. licheniformis* strain 21. *B. subtilis* strains 2084 and 27 were deposited on Mar. 8, 2007 and Jan. 24, 2008, respectively, at the Agricultural Research Service Culture Collection (NRRL), 1815 North University Street, Peoria, Ill., 61604 and given accession numbers NRRL B-50013 and NRRL B-50105, respectively. On Apr. 15, 2008, *B. licheniformis* strain 21 was deposited at NRRL and given accession number NRRL B-50134. All of these deposits were made under the provisions of the Budapest Treaty on the International Recognition of the Deposit of Microorganisms for the Purposes of Patent Procedure.

The compositions provided herein include *B. subtilis* strains 2084 and 27 and *B. licheniformis* strain 21 in an effective amount to control odors. In at least one embodiment of the composition, substantially equal amounts (based on colony forming units (cfu)) of each strain are used. However, differing amounts can also be used. For example, each strain can be added from about 10% to about 45% (based on cfu) of the total amount of strain in the composition. In an exemplary embodiment, *B. subtilis* strain 27 is included at 10%, *B. subtilis* strain 2084 is included at 45%, and *B. licheniformis* strain 21 is included at 45%.

In at least one embodiment of the composition, the total cfu of the *B. subtilis* strains 2084 and 27 and *B. licheniformis* strain 21 is from about $7.5 \times 10^7$ to about $7.5 \times 10^8$ in the final form of the composition. For example, about $2.5 \times 10^8$ total cfu of the *B. subtilis* strains 2084 and 27 and *B. licheniformis* strain 21 can be included in the final form of the composition.

In at least some embodiments of the composition, one or more water-soluble carrier, which is useful for rehydrating the strains, is added to the strains. In one embodiment, carriers include Baker's sugar, maltodextrin M100, and baylith. This embodiment, i.e., the three strains, *B. subtilis* strains 2084 and 27 and *B. licheniformis* strain 21, in substantially equal amounts (based on CFU) of each strain and the carriers, is referred to herein as FreshShield™ product. In at least some embodiments, FreshShield™ product is applied to animal bedding. This can be done during the manufacturing of bedding or at other times, as is explained in more detail below.

In another embodiment, carriers that bind ammonia are used. In one embodiment, these carriers include bentonite, Fuller's earth, mineral oil, and baylith. These carriers in combination with the three strains, *B. subtilis* strains 2084 and 27 and *B. licheniformis* strain 21, in substantially equal amounts (based on CFU) of each strain, Baker's sugar, and baylith are referred to herein as FreshShield™ stall treatment product. Other carriers, such as clintpolite, diamaceous earth, beolite clay, and limestone, also bind ammonia, and can also be used.

Making and Using the Compositions:

The *Bacillus* strains are grown in a liquid nutrient broth. In at least one embodiment, the *Bacillus* strains are grown to a level at which the highest number of spores are formed.

The *Bacillus* strains are produced by fermentation of the bacterial strains. Fermentation can be started by scaling-up a seed culture. This involves repeatedly and aseptically transferring the culture to a larger and larger volume to serve as the inoculum for the fermentation, which is carried out in large stainless steel fermentors in medium containing proteins, carbohydrates, and minerals necessary for optimal growth. A non-limiting exemplary medium is TSB. After the inoculum is added to the fermentation vessel, the temperature and agitation are controlled to allow maximum growth. Once the culture reaches a maximum population density, the culture is harvested by separating the cells from the fermentation medium. This is commonly done by centrifugation.

In one embodiment, to prepare the *Bacillus* strains, each *Bacillus* strain is fermented to a $5 \times 10^8$ CFU/ml to about $4 \times 10^9$ CFU/ml level. In at least one embodiment, a level of $2 \times 10^9$ CFU/ml is used. The bacteria are harvested by centrifugation, and the supernatant is removed. The pelleted bacteria can then be applied to the wood shavings. In at least come embodiments, the pelleted bacteria are freeze-dried and mixed with a carrier before they are applied to the wood shavings. However, it is not necessary to freeze-dry the *Bacillus* before using them. The strains can also be used with or without preservatives, and in concentrated, unconcentrated, or diluted form.

The count of the culture can then be determined. CFU or colony forming unit is the viable cell count of a sample resulting from standard microbiological plating methods. The term is derived from the fact that a single cell when plated on appropriate medium will grow and become a viable colony in the agar medium. Since multiple cells may give rise to one visible colony, the term colony forming unit is a more useful unit measurement than cell number.

To prepare compositions described herein, the cultures and carriers (where used) can be added to a ribbon or paddle mixer and mixed for about 15 minutes, although the timing can be increased or decreased. The components are blended such that a uniform mixture of the cultures and carriers result. The final product is preferably a dry, flowable powder.

In a non-limiting example of the FreshShield™ stall treatment product, the composition is applied to the surface on which an animal is kept, such as in an animal stall. For example, the composition is used as a topical treatment in a stall to treat wet spots. The FreshShield™ stall treatment product can be applied after wet bedding is removed. Clean bedding can be added on top of the FreshShield™ stall treatment product and mixed with the FreshShield™ stall treatment product. This treatment can be done on a daily basis, if desired, or more (or less) frequently.

In a non-limiting example of the FreshShield™ product, the compositions are added on to the bedding while the bedding is being manufactured, such as just prior to packaging. This provides the convenience of having bedding material that reduces odor and ammonia emissions and extends the bedding life.

In at least one embodiment of a method of making the FreshShield™ product, the bacteria are mixed into a liquid and applied onto bedding, such as wood shavings.

Different application rates of the three-strain combination for making the FreshShield™ product can be used. In at least one embodiment, the application rate for bedding for large animals (including, but not limited to, equine, bovine, ovine, and porcine) differs from the rate for bedding for small animals (including, but not limited to, hamster, rodents, guinea pig, rabbits, reptiles, dogs, and birds).

For example, for large animal bedding, a total of $2.9 \times 10^{10}$ total cfu of bacteria per cubic foot of wood shavings is used. The bacteria are added along with the carriers, M100 and Baker's sugar, to the wood shavings. However, the application rate can vary from $2.9 \times 10^8$ to $2.9 \times 10^{11}$ total cfu per cubic foot of wood shavings. In at least one embodiment, the *Bacillus* strains are at a concentration of $8.8 \times 10^{10}$ total cfu per gram of bacteria (each strain being ⅓ of this). In an exemplary embodiment, the *Bacillus* strains are combined with the wood shavings by mixing 10 kg of *Bacillus* with 55 gallons of water to form a stock solution. A total of 7 ml of stock solution is diluted with 53 ml of water and applied via an auger to one cubic foot of wood shavings prior to the bagging of the wood shavings. This diluted solution treats 10,000 bags of wood shavings, with one bag of shavings being approximately 3.0 cubic foot compressed and 9 cubic feet uncompressed. A typical horse stall (10'×10') uses 4 bags (3 cubic foot each) of shavings, which delivers $3.5 \times 10^{11}$ cfu/gram of *Bacillus* when applied as above.

In at least one embodiment, the application for small animal bedding is a total of $5.8 \times 10^{10}$ total cfu per cubic foot of wood shavings. The bacteria are added along with the carriers, M100 and Baker's sugar, to the wood shavings. However, the application rate can vary from $5.8 \times 10^9$ to $5.8 \times 10^{11}$ total cfu per cubic foot of wood shavings. In at least one embodiment, the *Bacillus* strains are at a concentration of $1.7 \times 10^{11}$ total cfu per gram of bacteria (each strain being ⅓ of this). In at least some embodiments, the *Bacillus* combination is added to the wood shavings by mixing 10 kg of *Bacillus* with 55 gallons of water to form a stock solution. In an exemplary embodiment, 7 ml of stock solution is diluted with 53 ml of water and applied to one cubic foot of wood shavings as they are being conveyed via an auger prior to bagging of the wood shavings. This diluted solution treats the equivalent of 30,000-10,000 bags of wood shavings, with one bag of shavings being approximately 1-3 cubic foot compressed and 3-9 cubic feet uncompressed, respectively. Small animal bedding materials come in a variety of sizes. Any dilution that would achieve a desired cfu per cubic foot is suitable within the scope of this invention.

An exemplary composition of FreshShield™ product is shown below in Table 1.

TABLE 1

| Ingredient | Amount added | % composition by weight |
|---|---|---|
| *B. licheniformis* 21 at $3.8 \times 10^{11}$ cfu/g | 0.925 kg | 2.70* |
| *B. subtilis* 27 at $3.0 \times 10^{11}$ cfu/g | 1.172 kg | 9.50* |
| *B. subtilis* 2084 at $2.0 \times 10^{11}$ cfu/g | 1.764 kg | 3.53* |
| Baker's sugar | 3.069 kg | 42.13 |
| Maltodextrin M100 | 3.008 kg | 41.29 |
| Baylith | 0.061 kg | 0.85 |
| Total | 10 kg | 100% |

*This is for a specific lot of *Bacillus*. The amount added varies depending on the concentration of bacteria.

An exemplary composition of FreshShield™ stall treatment product is shown below in Table 2.

TABLE 2

| Ingredient | Amount added | % composition by weight |
|---|---|---|
| *B. licheniformis* 21 at $5.0 \times 10^{11}$ cfu/g | 0.001 kg | 0.02* |
| *B. subtilis* 27 at $5.0 \times 10^{11}$ cfu/g | 0.001 kg | 0.02* |
| *B. subtilis* 2084 at $5.0 \times 10^{11}$ cfu/g | 0.001 kg | 0.02* |
| Bentonite | 3.176 kg | 69.75 |
| Fullers Earth | 1.361 kg | 29.886 |

TABLE 2-continued

| Ingredient | Amount added | % composition by weight |
|---|---|---|
| Mineral Oil | 0.009 kg | 0.197 |
| Baylith | 0.005 kg | 0.109 |
| Total | 4.554 kg | 100% |

*This is for a specific lot of Bacillus. The amount added varies depending on the concentration of bacteria.

Additional uses of the compositions include the following. The composition can be added to as an ingredient to existing stall treatment products as an all-natural additive for further odor control. The compositions can also be used with alternative bedding products, e.g., corn cob bedding, paper bedding, straw, and wood pellets, used in the small and large animal market. For use with alternative bedding products, the compositions are applied as is described above for wood shavings or in other ways.

Further uses of the compositions include using them on an absorbent material, such as granulated clay, for covering the floor of an animal's cage or excretory box. For example, the compositions can be used as a litter additive for cat litter boxes and litter boxes for other animals. In one embodiment of the litter additive, B. subtilis strains 2084 and 27 and B. licheniformis strain 21 and carriers are combined. In an exemplary embodiment, bentonite, Fuller's earth, mineral oil, and baylith are the carriers. The cat litter additive can have the same formula as shown in Table 2 or it can have a different formula. The cat litter additive can be applied to cat litter as needed for odor control. The cat litter additive can also be used as an ingredient for litter manufacturing or as a topical treatment.

Routine use of the one or more compositions provided herein can dramatically reduce and even eliminate animal odors. The compositions are ecologically friendly products because instead of chemicals, bacteria are used to control animal odors. The compositions are considered "green," that is, something good for the environment. The compositions are all natural and safe. The compositions are highly stable, therefore, they have a long shelf life. In addition, the compositions extend bedding life. This is increasingly important as wood and other bedding sources are becoming more expensive and more difficult to obtain. When one or more compositions is added to animal bedding, the treated bedding is easy to use because nothing extra needs to be added to the bedding for odor control. The compositions also provide a healthier living environment for animals living on bedding or other surfaces treated with one or more composition. Animals do not like living in ammonia-rich environments. Ammonia burns their eyes and causes other problems such as respiratory problems. Therefore, reductions in ammonia and other odors improve the animal's quality of life. In addition, more efficient composting of animal manure is accomplished by using the compositions provided herein.

A healthier working environment is provided for workers that train and take care of animals. For instance, ammonia, which irritates the people's lungs and can cause respiratory and other problems, is reduced.

The compositions can be easily applied to wood shavings. It also provides a surface for the Bacillus bacteria to live. Unlike simply adding untreated wood shavings, wood shavings treated with a composition provided herein adds the waste digesting power of the Bacillus bacteria, which reduces the odor and ammonia.

Although not intended to be a limitation to the present disclosure, it is believed that inhibition of odors is accomplished via reduced volatilization of ammonia through controlled decomposition of nitrogen-containing compounds and utilization of the nitrogen by the Bacillus strains. Where used, the carriers limestone, clay, zeolite, diatomaceous earth, clintpolite, bentonite, and Fuller's earth, also bind ammonia and therefore reduce odors.

EXAMPLES

The following Examples are provided for illustrative purposes only. The Examples are included herein solely to aid in a more complete understanding of the presently described invention. The Examples do not limit the scope described herein described or claimed herein in any fashion.

Example 1

Overview: This research was conducted to determine the effectiveness of a horse waste product at lessening the odor associated with waste excretion in confined areas such as the common equine box stall.

Protocol: 12 horses housed in a barn were utilized to "soil" the stalls. Horses/stalls were blocked by age/ration/sex so that there were similar types of horses within each treatment. Horses were stalled for approximately 12 hours/day with daily turnout. The treatments were as follows: Control: Consisted of normal bedding practices per the protocols of the facility with 6 stalls and Bedding Treatment: In addition to normal bedding protocols, a top dress of a "horse waste product" applied to shavings was applied to selected stalls with 6 stalls. Bedding treatment was applied by spreading 1 (one) scoop (in this example, one (1) scoop equals $8.64 \times 10^{10}$ total cfu of the Bacillus strains) of treatment material, which is prepared to contain $2.4 \times 10^8$ total cfu/g of B. subtilis strains 2084 and 27 and B. licheniformis strain 21 bacteria provided in FreshShield™ product, that is, one scoop per 1 bag (2.0 cubic foot) of Marth Easy Pick™ shavings.

The trial initiation had a 3 week trial period. At the beginning of the trial all stalls were cleaned out of all waste and bedding material.

Control stalls were re-bedded with 7 bags each of untreated Marth Easy Pick Shavings. Treated stalls had 7 scoops of FreshShield™ product on 7 Marth Easy Pick™ 2.0 cubic foot bags of wood shavings, applied and thoroughly mixed in the bedding. Treated stalls were uniquely marked so farm personnel could easily identify treatment stalls. For the remainder of the trial, bedding protocols were adhered to per the facility managers direction. One scoop of FreshShield™ product was applied per bag of fresh shaving material put down in the stall. Fresh FreshShield™ product was mixed in with fresh shavings at time of application. Individual stall records were maintained regarding the amount of fresh bedding put down in each stall on a daily basis. The amount of deodorizer, such as Sweet PDZ or Stall Dry, was applied daily was recorded.

Results: The FreshShield™ product reduced odors in the treated stalls of the barn. The test was done during the time of year that the barn was open. The FreshShield™ product reduced stall odors and ammonia smells, making the facility and environment better for the horses.

Example 2

Aim: To determine if FreshShield™ product will modulate the decomposition of manure mixed with Marth Easy Pick™ Bedding over time. This model utilized cow urine and cow fecal material.

Protocol: A waste in vitro model was prepared by placing 100 g of Marth Easy Pick™ bedding into each of fifteen 6"×9"×3" Ziploc™ containers with a small hole drilled in one end. The hole was taped to reseal the container. 500 ml of freshly collected cow urine was added to each container followed by 50 g of freshly collected cow fecal matter. Three treatments were designated across the 15 containers with 5 replicates/treatment. Treatments consisted of control, containing no FreshShield™ product, and FreshShield™ product added at a 1× dose and a 2× dose. The 1× dose contained $3.12 \times 10^9$ CFU of the three *Bacillus* strains, i.e., *B. subtilis* strains 2084 and 27 and *B. licheniformis* strain 21, with the 2× dose containing twice that amount. After addition of all materials to the Ziploc containers, contents of the containers were thoroughly mixed using a plastic teaspoon, with different spoons used to mix each treatment. Ziploc containers were sealed by placing the lid on top and placed in the Bio-Cold environmental chamber set at 81° F. and 55% humidity.

Ammonia measurements were taken from each container at 24 hours, 48 hours, and 7 days after placement in the Bio-Cold chamber. Measurements were taken using the Drager pump fitted with disposable ammonia tubes.

Results: Ammonia concentrations at 48 hours can be seen in FIG. 1. Results from ammonia concentration after 7 days were also observed. There was no significant difference between treatments at 24 hours. At 48 hours the 2× dose was significantly less than that of the control, but not significantly different for the 1× dose. The 1× dose was less than that of the control but not significant. There were no significant differences between treatment groups after seven days.

Example 3

Study Details: The following study was performed to show the effect of bedding containing the FreshShield™ product and having Baker's sugar, maltodextrin M100, and baylith as the carriers (formulated as shown in Table 1 above) and bedding treated with FreshShield™ stall treatment product having bentonite, Fuller'earch, mineral oil, and baylith as the carriers (formulated as shown in Table 2 above) to determine the effect of carriers on the ability of the product to control ammonia production. Both products included the three strains, *B. subtilis* strains 2084 and 27 and *B. licheniformis* strain 21, as shown in Tables 1 and 2. Soiled horse bedding material collected from a stable was placed into sealed containers. Treatments were applied at a rate of $1.0 \times 10^{10}$ total cfu of the three strains of the bacteria in the FreshShield™ product per 500 grams of soiled bedding and at a rate of $10 \times 10^{10}$ total cfu of the three strains of bacteria in the FreshShield™ stall treatment product. Ammonia measurements were taken at time 0, 6, and 16 hours post-treatment using a Draeger ammonia detector.

Figure 2:
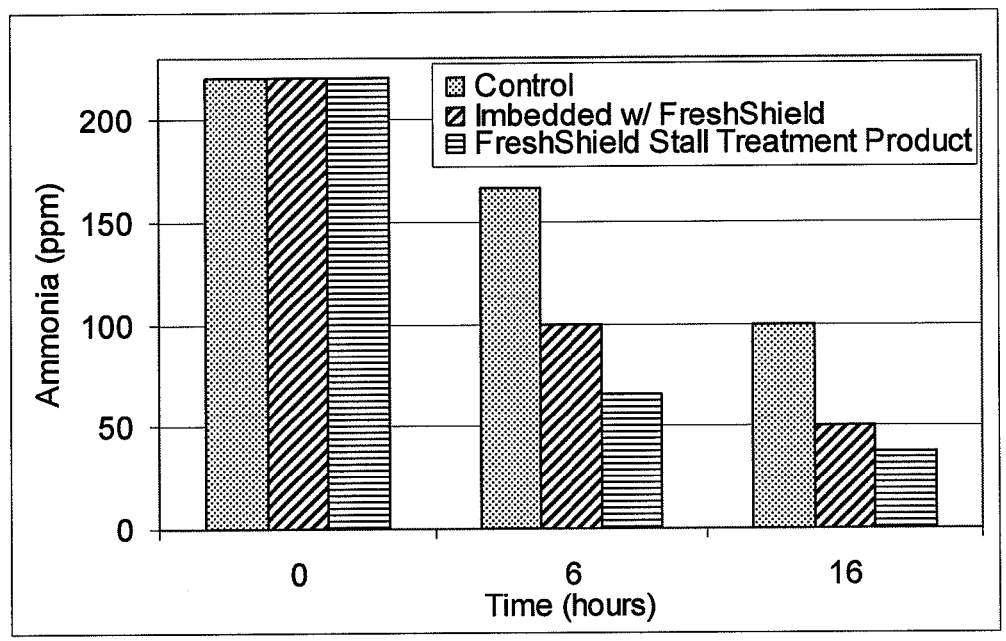
FIG. 2 is a graph of the reduction in ammonia levels in bedding with FreshShield™ product or FreshShield™ stall treatment product.

Results: FIG. 2 shows an average ammonia reduction of 50% in bedding with FreshShield™ product and 62% in bedding with FreshShield™ stall treatment product.

Example 4

Study Details The following study was performed to show the effect of FreshShield™ product on ammonia production in soiled pea gravel. Soiled pea gravel was placed into sealed containers. The composition of the FreshShield™ product is shown in Table 3 below. Control samples received no FreshShield™ product. Treatments were applied as in Example 3 for the FreshShield™ stall treatment product. A smell panel evaluated the ammonia odors over time. Ammonia measurements were taken at 1 week post-treatment using a Draeger ammonia detector.

TABLE 3

| Ingredient | Amount added | % composition by weight |
| --- | --- | --- |
| *B. licheniformis* 21 at $5.0 \times 10^{11}$ cfu/g | 0.001 kg | 0.02* |
| *B. subtilis* 27 at $5.0 \times 10^{11}$ cfu/g | 0.001 kg | 0.02* |
| *B. subtilis* 2084 at $5.0 \times 10^{11}$ cfu/g | 0.001 kg | 0.02* |
| Rice hulls | 4.546 kg | 69.75 |
| Baylith | 0.005 kg | 0.109 |
| Total | 4.554 kg | 100% |

Figure 3:
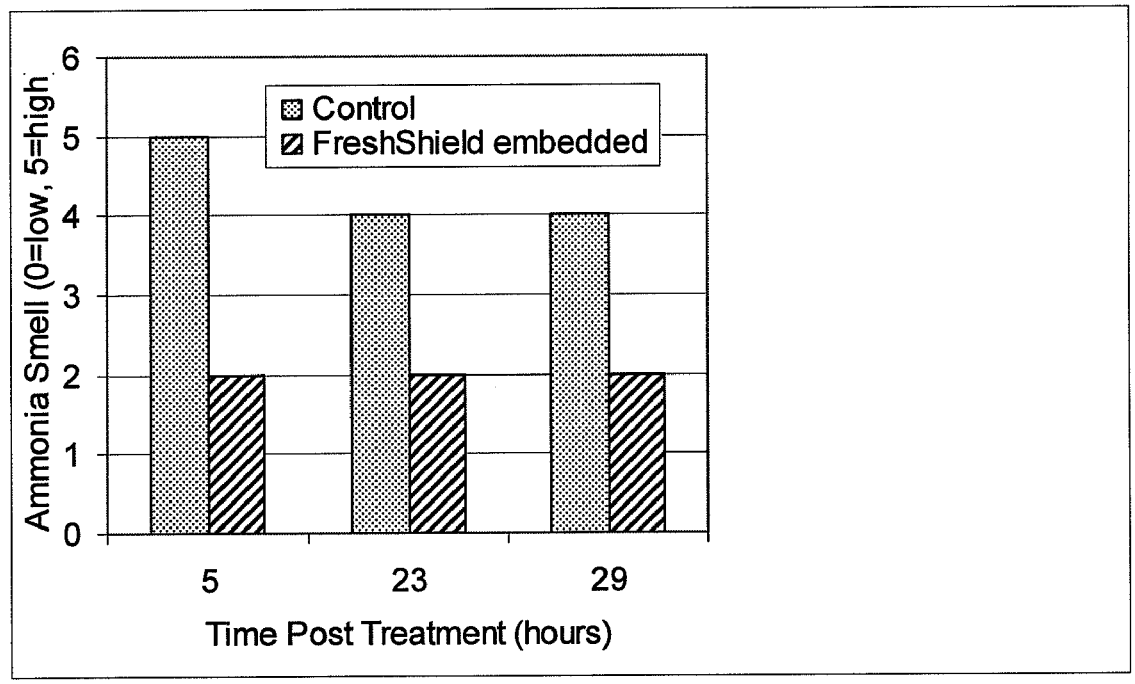
FIG. 3 is a graph of smell panel results after 5, 23, and 29 hours, showing reduction in ammonia smell with FreshShield™ product treatment.
Figure 4:
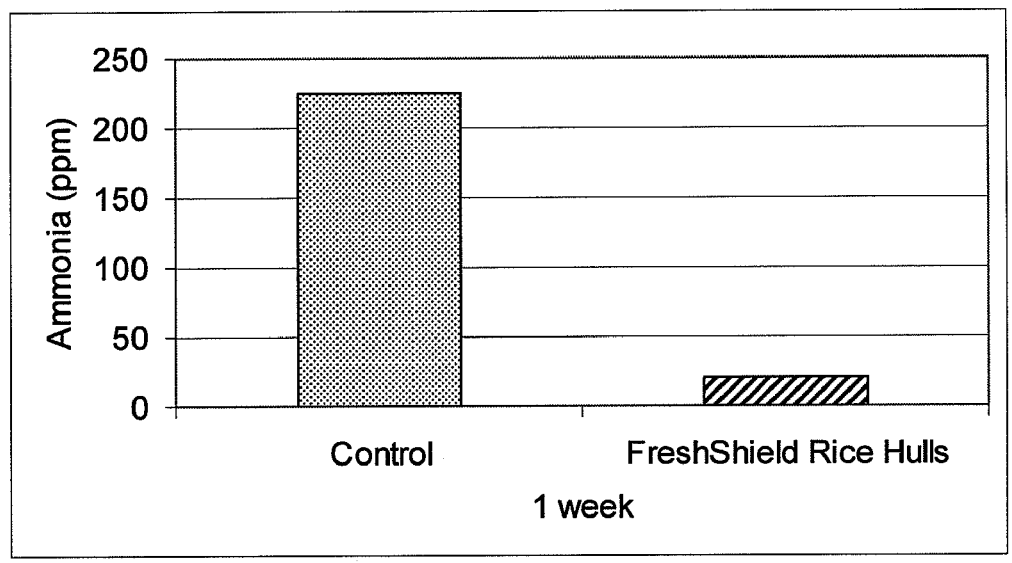
FIG. 4 is a graph showing the reduction in ammonia after one week of FreshShield™ product treatment.

Results: The smell panel noted a marked reduction in ammonia smell with FreshShield™ product, at least a 50% reduction at 5, 23, and 29 hours after initial treatment as compared to the control samples (FIG. 3). The reduction in measurable ammonia was seen after one week of treatment, and no noticeable ammonia odors were present. In comparison, after one week the control containers still had offensive levels of ammonia. FIG. 4 shows that after one week, the average ammonia levels were 225 ppm for the control and less than 20 ppm in the treated containers.

Example 5

Initial Visit: A commercial guinea pig farm tested the FreshShield™ product at rates of $1.45 \times 10^{10}$ total cfu per cubit foot of bedding (0.5×), $2.9 \times 10^{10}$ total cfu per cubic foot of bedding (1.0×) and $5.8 \times 10^{10}$ total cfu per cubic foot of bedding (2.0×), to measure ammonia reduction within a guinea pig commercial facility. The FreshShield™ product included the three strains of bacteria, *B. subtilis* strains 2084 and 27 and *B. licheniformis* strain 21. During the initial visit, control samples were collected from pens that were to be treated and used within the experiment. For each of nine pens, one composite sample was formed by collecting the same quantity from a similar location in each pen and combining it into one sample bag.

Forty-eight hours after collection, ammonia readings were taken and recorded. After composite samples were collected, the appropriate concentration of product to be tested was applied to clean fresh bedding. $1.45 \times 10^{10}$ total cfu per cubic foot of bedding (0.5×), $2.9 \times 10^{10}$ total cfu per cubic foot of bedding (1.0×) and $5.8 \times 10^{10}$ total cfu per cubic foot of bedding (2.0×), by spraying the concentrated liquid on to the clean bedding. Treatments included a control (no FreshShield™ product), 0.5× FreshShield™ product, 1.0× FreshShield™ product, and 2× FreshShield™ product. Guinea pigs were allowed to maintain normal living conditions on treated bedding.

Follow-up Visit: One week following the initial treatment of bedding treated with the *Bacillus* shaving product, used bedding samples were collected. Again, the same quantity of bedding from similar locations was collected from each pen. Three pens were combined into one composite sample. Three replicate composite samples were collected and combined for each treatment. Forty-eight hours after collection ammonia readings were taken and recorded.

Figure 5:
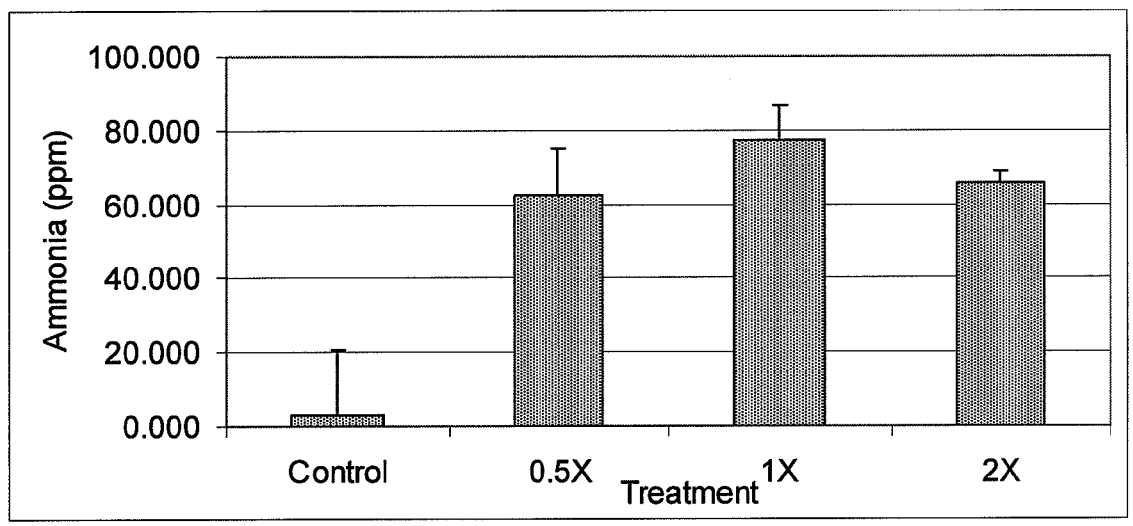
FIG. 5 is a graph showing the difference in reduction of ammonia levels from used guinea pig bedding after 7 days of treatments at different concentrations of FreshShield™ product compared to after 7 days with no treatment.

Results: The results show that ammonia readings from used guinea pig bedding with no treatment were higher than ammonia readings from used guinea pig bedding containing 0.5×, 1× and 2× *Bacillus* treatment levels. The difference between non-treated and treated bedding taken from the same pens after 7 days of treatment were decreased compared to the control difference, as shown in FIG. 5.

Example 6

The Problem

Ammonia negatively affects the health of stabled horses worldwide. Even long-term, low level exposure to ammonia can affect a horse's respiratory health, immune response, and the health of those people working in and around horses. FreshShield is an all natural, product that proactively stops ammonia production. The active ingredient in FreshShield stall treatment product starts working when applied to urine and/or feces to reduce harmful ammonia emissions. There are a number of stall treatment products available, but most work by masking the ammonia only for a short time and not by attacking the underlying cause of high ammonia.

Study Details

The following study was performed to compare the effect of FreshShield™ stall treatment product on ammonia production to three other stall treatment products: Stall Fresh, Stall DRY Plus, and Sweet PDZ stall treatment products. Soiled horse bedding collected from a stable was placed into sealed containers. The FreshShield™ stall treatment product was formulated as in Table 1 above.

Treatments of the FreshShield™ stall treatment product were applied by applying 4 oz. of the product daily. The other products were applied according to each of their label directions. Ammonia measurements were taken at time 0 and 24 hours post-treatment using a Draeger ammonia detector.

The Results

Figure 6:
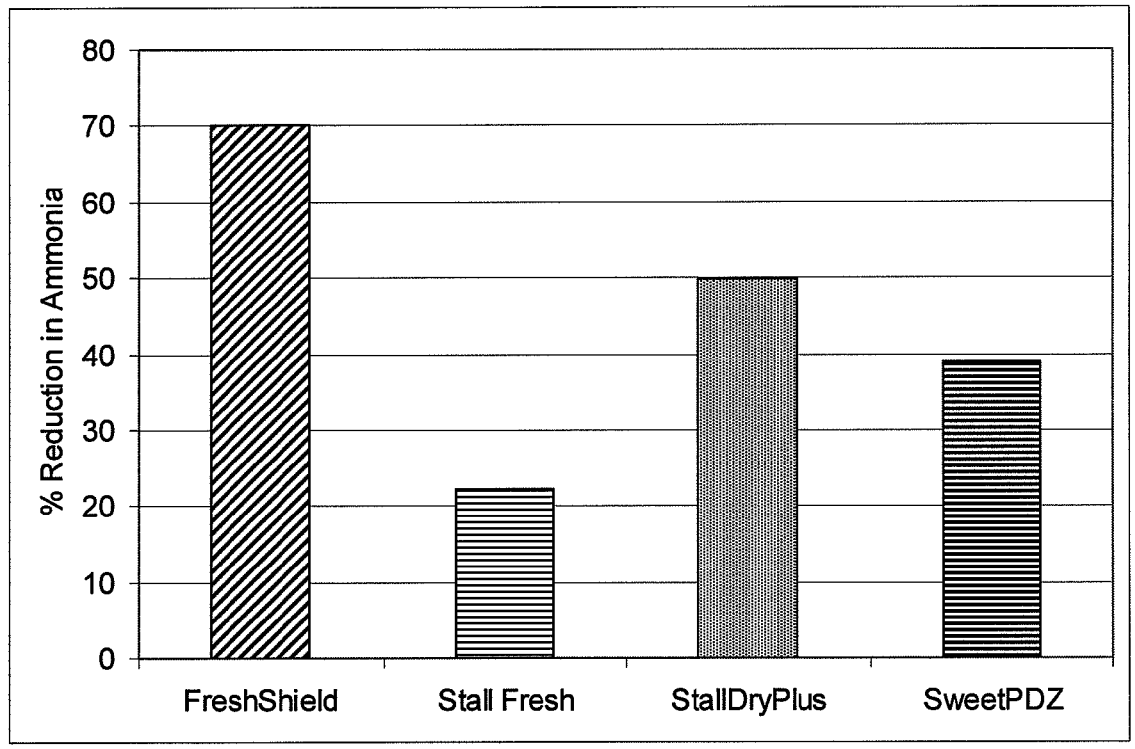
FIG. 6 is a graph showing reductions in ammonia levels after 24 hours in manure treated with FreshShield stall treatment product, Stall Fresh stall treatment product, Stall DRY Plus stall treatment product, and Sweet PDZ stall treatment product.

As is shown in FIG. 6, after 24 hours, ammonia was reduced by 70% in manure treated with FreshShield stall treatment product, by 22.2% in manure treated with Stall Fresh stall treatment product, by 49.8% in manure treated with Stall DRY Plus stall treatment product, and by 38.9% in manure treated with Sweet PDZ stall treatment product. The other products worked initially, but then lost their effectiveness over time. FreshShield stall treatment product kept working long after the other products stop. FreshShield stall treatment product worked well with both high and low initial ammonia levels, and reduced the ammonia by the greatest amount overall.

It is understood that the various preferred embodiments are shown and described above to illustrate different possible features described herein and the varying ways in which these features may be combined. Apart from combining the different features of the above embodiments in varying ways, other modifications are also considered to be within the scope described herein. The invention is not intended to be limited to the preferred embodiments described above.

It is specifically intended that the present invention not be limited to the embodiments and illustrations contained herein, but include modified forms of those embodiments including portions of the embodiments and combinations of elements of different embodiments as come within the scope of the following claims.

What is claimed is:

1. A composition comprising:
   an isolated *Bacillus subtilis* 2084 (NRRL B-50013) or an isolated strain having all of the identifying characteristics of the *Bacillus subtilis* 2084 (NRRL B-50013);
   an isolated *B. subtilis* 27 (NRRL B-50105) or an isolated strain having all of the identifying characteristics of the *B. subtilis* 27 (NRRL B-50105); and
   an isolated *B. licheniformis* 21 (NRRL B-50134) or an isolated strain having all of the identifying characteristics of the *B. licheniformis* 21 (NRRL B-50134).

2. The composition of claim 1, wherein the amount of each strain is about the same.

3. The composition of claim 1, further comprising at least one carrier capable of binding ammonia.

4. The composition of claim 3, wherein the carrier is selected from the group consisting of comprise limestone, clay, zeolite, diatomaceous earth, clintpolite, bentonite, and Fuller's earth.

5. A method of controlling odors and ammonia from animal waste, the method comprising applying the composition of claim 3 to an area where an animal is housed, wherein application of the composition controlling odors and ammonia in the animal waste.

6. The composition of claim 1, further comprising at least one water-soluble carrier.

7. The composition of claim 6, wherein the carrier is selected from the group consisting of Baker's sugar, maltodextrin M100, and baylith.

8. The composition of claim 1, further comprising bentonite, Fuller's earth, mineral oil, and baylith.

9. The composition of claim 1, further comprising an absorbent material.

10. A composition comprising:
    an isolated *Bacillus subtilis* 2084 (NRRL B-50013) or an isolated strain having all of the identifying characteristics of the *Bacillus subtilis* 2084 (NRRL B-50013);
    an isolated *B. subtilis* 27 (NRRL B-50105) or an isolated strain having all of the identifying characteristics of the *B. subtilis* 27 (NRRL B-50105);
    an isolated *B. licheniformis* 21 (NRRL B-50134) or an isolated strain having all of the identifying characteristics of the *B. licheniformis* 21 (NRRL B-50134); and
    an absorbent material, wherein the absorbent material is cat litter.

11. An animal bedding comprising:
    an isolated *Bacillus subtilis* 2084 (NRRL B-50013) or an isolated strain having all of the identifying characteristics of the *Bacillus subtilis* 2084 (NRRL B-50013);
    an isolated *B. subtilis* 27 (NRRL B-50105) or an isolated strain having all of the identifying characteristics of the *B. subtilis* 27 (NRRL B-50105);
    an isolated *B. licheniformis* 21 (NRRL B-50134) or an isolated strain having all of the identifying characteristics of the *B. licheniformis* 21 (NRRL B-50134); and
    animal bedding.

12. The animal bedding of claim 11, wherein the animal bedding is selected from the group consisting of wood shavings, corn cob bedding, paper bedding, straw, and wood pellets.

13. The animal bedding of claim 11, further comprising at least one water-soluble carrier.

14. A method of controlling odors and ammonia from animal waste, the method comprising applying the animal bedding of claim 11 to an area where an animal is housed, wherein application of the composition controlling odors and ammonia in the animal waste.

15. A method of making animal bedding, the method comprising applying *Bacillus subtilis* 2084 (NRRL B-50013) or a strain having all of the identifying characteristics of the *Bacillus subtilis* 2084 (NRRL B-50013), *B. subtilis* 27 (NRRL B-50105) or a strain having all of the identifying characteristics of the *B. subtilis* 27 (NRRL B-50105), and *B. licheni-*

*formis* 21 (NRRL B-50134) or a strain having all of the identifying characteristics of the *B. licheniformis* 21 (NRRL B-50134) to animal bedding.

16. The method of claim 15, further comprising:
adding a water-soluble carrier to the strains; and
rehydrating the strains, wherein the rehydrated strains are applied to the animal bedding.

17. The method of claim 15, wherein the strains are applied to provide substantially the same cfu of each strain.

18. The method of claim 15, further comprising packaging the animal bedding, wherein the strains are applied prior to packaging the animal bedding.

19. The method of claim 15, wherein the animal bedding is selected from the group consisting of wood shavings, corn cob bedding, paper bedding, straw, and wood pellets.

20. A method of making a composition, the method comprising:
combining *Bacillus subtilis* 2084 (NRRL B-50013) or a strain having all of the identifying characteristics of the *Bacillus subtilis* 2084 (NRRL B-50013) with *B. subtilis* 27 (NRRL B-50105) or a strain having all of the identifying characteristics of the *B. subtilis* 27 (NRRL B-50105), and with *B. licheniformis* 21 (NRRL B-50134) or a strain having all of the identifying characteristics of the *B. licheniformis* 21 (NRRL B-50134) to form the three-strain composition.

21. The method of claim 20, further comprising freeze drying each strain.

22. The method of claim 21, further comprising adding the freeze-dried strain to at least one water-soluble carrier.

23. The method of claim 21, further comprising adding the freeze-dried strain to at least one carrier that is capable of binding ammonia.

\* \* \* \* \*

UNITED STATES PATENT AND TRADEMARK OFFICE
CERTIFICATE OF CORRECTION

| | | |
|---|---|---|
| PATENT NO. | : 8,025,874 B2 | Page 1 of 1 |
| APPLICATION NO. | : 12/425546 | |
| DATED | : September 27, 2011 | |
| INVENTOR(S) | : Marianne Cain Bellot, Keith J. Mertz and Thomas G. Rehberger | |

It is certified that error appears in the above-identified patent and that said Letters Patent is hereby corrected as shown below:

Column 12, line 9 delete "comprise"

Column 12, line 15 replace "controlling" with --controls--

Signed and Sealed this

Thirty-first Day of January, 2012

David J. Kappos
*Director of the United States Patent and Trademark Office*